United States Patent
Scheuch et al.

(10) Patent No.: US 7,766,012 B2
(45) Date of Patent: Aug. 3, 2010

(54) DEVICE FOR THE CONTROLLED INHALATION OF THERAPEUTIC AEROSOLS

(75) Inventors: Gerhard Scheuch, Gemuenden (DE); Thomas Meyer, Poecking (DE); Knut Sommerer, Munich (DE); Axel Greindl, Valley (DE); Bernhard Müllinger, Unterdietfurt (DE)

(73) Assignee: Activaero GmbH, Gemuenden (DE)

( * ) Notice: Subject to any disclaimer, the term of this patent is extended or adjusted under 35 U.S.C. 154(b) by 0 days.

(21) Appl. No.: 09/810,988

(22) Filed: Mar. 16, 2001

(65) Prior Publication Data

US 2001/0037806 A1 Nov. 8, 2001

(30) Foreign Application Priority Data

Mar. 17, 2000 (DE) ............... 100 13 093

(51) Int. Cl.
*A61M 15/08* (2006.01)
*A61M 11/08* (2006.01)

(52) U.S. Cl. .................. 128/203.21; 128/200.12; 128/200.21; 128/203.12; 128/203.15; 128/203.23; 128/205.13; 128/205.21

(58) Field of Classification Search ............ 128/200.14, 128/200.23, 203.12, 204.18, 204.21, 204.23, 128/204.26, 205.23, 207.14, 207.18, 200.24, 128/203.14, 203.15, 203.23, 203.18, 203.21, 128/200.11; 239/338, 373
See application file for complete search history.

(56) References Cited

U.S. PATENT DOCUMENTS

| | | | |
|---|---|---|---|
| 4,495,944 A | 1/1985 | Brisson et al. | 128/725 |
| 4,984,158 A | 1/1991 | Hillsman | 364/413.04 |
| 4,988,146 A | 1/1991 | Weihrauch | |
| 5,156,776 A * | 10/1992 | Loedding et al. | 261/27 |
| 5,161,524 A * | 11/1992 | Evans | 128/203.15 |
| 5,167,506 A | 12/1992 | Kilis et al. | 434/262 |
| 5,363,842 A | 11/1994 | Mishelevich et al. | 128/200.14 |
| 5,392,768 A * | 2/1995 | Johansson et al. | 128/200.14 |
| 5,404,871 A | 4/1995 | Goodman et al. | 128/200.14 |
| 5,415,161 A * | 5/1995 | Ryder | 128/200.23 |
| 5,452,711 A | 9/1995 | Gault | 128/200.14 |
| 5,490,502 A * | 2/1996 | Rapoport et al. | 128/204.23 |
| 5,542,410 A * | 8/1996 | Goodman et al. | 128/200.14 |
| 5,551,416 A | 9/1996 | Stimpson et al. | 128/200.16 |
| 5,560,353 A * | 10/1996 | Willemot et al. | 128/204.21 |

(Continued)

FOREIGN PATENT DOCUMENTS

EP 0 965 355 A2 12/1999

OTHER PUBLICATIONS

Institut for Aerosol Medicin article on AKITA a fully electronically regulated device for aerosols (German acronym), http://www.inamed.de/akitacontente.htm, Mar. 16, 2001.

(Continued)

*Primary Examiner*—Justine R Yu
*Assistant Examiner*—Clinton Ostrup
(74) *Attorney, Agent, or Firm*—Brown & Michaels, PC

(57) ABSTRACT

A device for the controlled inhalation of therapeutic aerosols comprises means providing individual patient parameters and/or aerosol parameters for the inhalation. The aerosol doses, such as the tidal volume and the respiratory flow, are individually adjusted on the basis of these individual parameters. Thus, the inhalation device may be individually adjusted to the patient to be treated.

17 Claims, 3 Drawing Sheets

U.S. PATENT DOCUMENTS

| | | | | |
|---|---|---|---|---|
| 5,598,838 | A * | 2/1997 | Servidio et al. | 128/204.23 |
| 5,608,647 | A * | 3/1997 | Rubsamen et al. | 700/281 |
| 5,687,717 | A * | 11/1997 | Halpern et al. | 600/300 |
| 5,809,997 | A * | 9/1998 | Wolf | 128/200.23 |
| 5,813,397 | A * | 9/1998 | Goodman et al. | 128/200.14 |
| 5,830,490 | A | 11/1998 | Weinstein et al. | 424/405 |
| 5,842,468 | A * | 12/1998 | Denyer et al. | 128/200.23 |
| 5,931,160 | A * | 8/1999 | Gilmore et al. | 128/204.21 |
| 5,950,619 | A | 9/1999 | Vam der Linden et al. | 128/200.16 |
| 6,024,089 | A * | 2/2000 | Wallace et al. | 128/204.21 |
| 6,116,233 | A * | 9/2000 | Denyer et al. | 128/200.18 |
| 6,148,815 | A * | 11/2000 | Wolf | 128/205.23 |
| 6,202,642 | B1 | 3/2001 | McKinnon et al. | 128/200.23 |
| 6,269,810 | B1 * | 8/2001 | Brooker et al. | 128/203.12 |
| 6,435,175 | B1 * | 8/2002 | Stenzler | 128/200.14 |
| 6,606,989 | B1 * | 8/2003 | Brand et al. | 128/200.16 |

OTHER PUBLICATIONS

Bennett, William D., Controlled inhalation of aerosolised therapeutics, Expert Opin. Drug Deliv., 2005, pp. 763-767, vol. 2, iss. 4, Ashley Publications Ltd., London, England.

Brand, P., et al., Total Deposition of Therapeutic Particles During Spontaneous and Controlled Inhalations, Journal of Pharmaceutical Sciences, Jun. 2000, pp. 724-731, vol. 89, iss. 6, Wiley-Liss, Inc., Wilmington, DE.

Koehler, Elke, et al., Lung Deposition after Electronically Breath-Controlled Inhalation and Manually Triggered Conventional Inhalation in Cystic Fibrosis Patients, Journal of Aerosol Medicine, 2005, pp. 386-395, vol. 18, iss. 4, Mary Ann Lieber, Inc., New Rochelle, NY.

Giraud, V. and Roche, N. "Misuse of Corticosteroid Metered-Dose Inhaler is Associated With Decreased Asthma Stability" European Respiratory Journal, 19, p. 246-251. 2002.

* cited by examiner

Principle of operation of the AKITA

1 Compressed Air
2 Pressure Reduction
3 Valve
4 Inhalation flow rate constanter
5 Vaporiser

DEVICE FOR THE CONTROLLED INHALATION OF THERAPEUTIC AEROSOLS

FIELD OF THE INVENTION

The present invention relates to a device and a method for the controlled inhalation of therapeutic aerosols and in particular for the individual dosimetry of inhaleable aerosols.

BACKGROUND OF THE INVENTION

In the inhalation of drugs in form of aerosols, several factors are of importance for the deposition of the active ingredient in the lung. The deposition of the active ingredient in the lung depends on the particle properties of the active ingredient to be inhaled, such as the particle size, electric charge and hygroscopicity, the inhalation velocity (i.e. respiratory flow) of the patient and the inhalation depth (i.e. tidal volume) of a breath of the patient to be treated.

In various drugs which are to be inhaled in form of aerosols, the amount of inhaled active ingredient has to be given in extremely accurate doses since any overdose could be critical to the patient. In case of conventional inhalation methods, the particle size is adapted to the drug to be administered. However, the patient's breathing pattern is not controlled in any way so that the individual dosage may vary strongly. In case of weak breathing (shallow, rapid respiration), the inhaled drug falls short of the recommended dose, whereas heavy breathing (deep, slow respiration) results in an overdose.

EP-B-0 587 380 describes a drug delivery arrangement that recognizes an inhalation and administers the drug only during an inhalation phase of the breathing cycle while the patient is free to breathe as he likes. This freedom, however, varies from patient to patient, so that the dosages vary considerably. EP-A-0 965 355 describes a controlled inhalator with a predetermined aerosol volume and a limitation of the respiratory flow. In this inhalator, the respiratory flow and the tidal volume are adjusted within certain limits. However, as a mass product, this inhalator cannot be adapted to the concrete requirements as to the pulmonary function of a specific individual. The parameters adjusted for the tidal volume and the respiratory flow are acceptable for the majority of patients, however, the drug administration for the individual patient is not optimal.

Therefore, the following problems occur in practice:

1. Many very obstructive patients are no longer capable of developing the necessary respiratory flow which they would, however, have to develop for an optimal aerosol application;
2. Many of these patients have only very restricted tidal volumes, above all patients with pulmonary emphysema or patients with very small lung volumes;
3. Every patient inhales at a different rate and with a different volume so that the drug dosage within the lung varies widely.

It is the object of the present invention to provide an improved device for a controlled inhalation of therapeutic aerosols.

DRAWINGS

DESCRIPTION OF THE INVENTION

Figure 1:
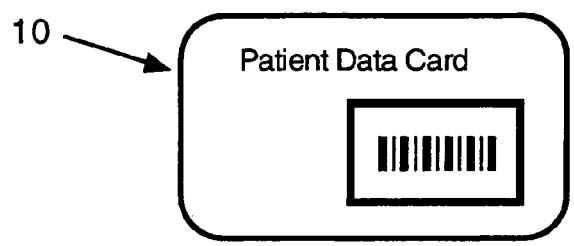
FIG. 1 is a schematic plan view of a programmable memory card for holding patient information.
Figure 2:
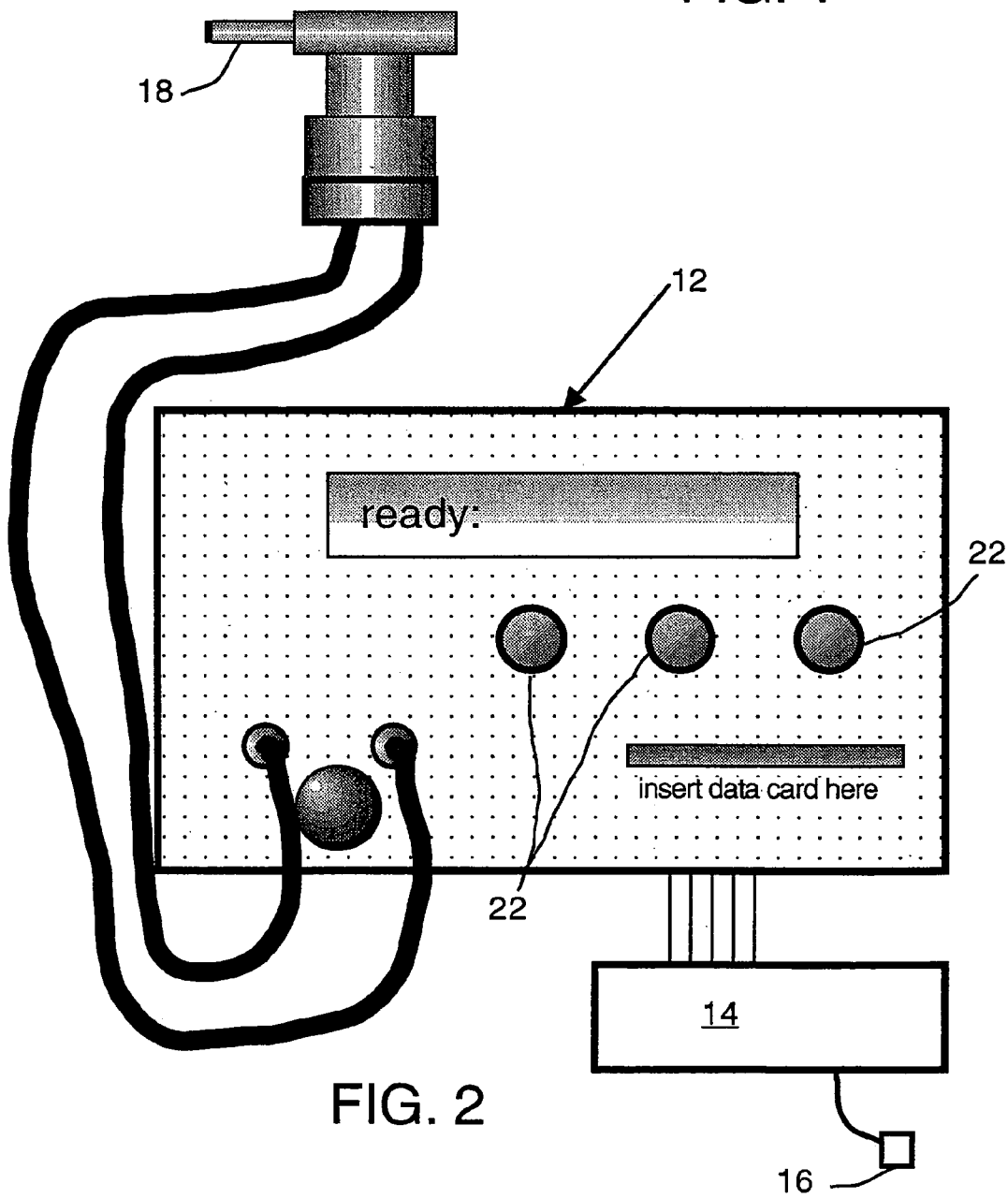
FIG. 2 is a diagram of my inhaler device for accommodating the respiratory characteristics of different patients.
Figure 3:
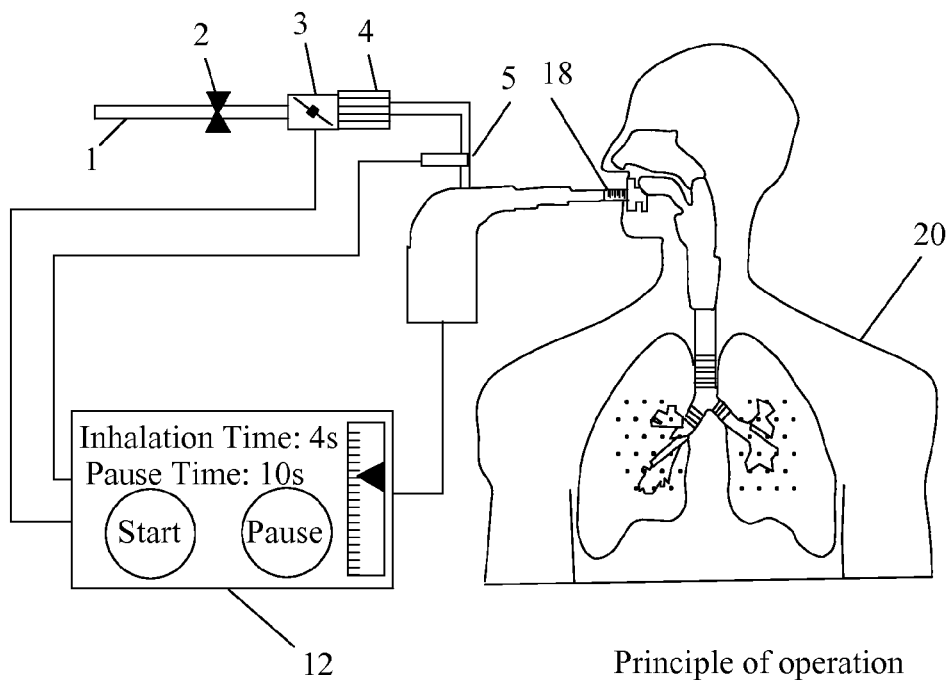
FIG. 3 is a diagram showing the adjustment of flow rates for an individual patient.
Figure 4:
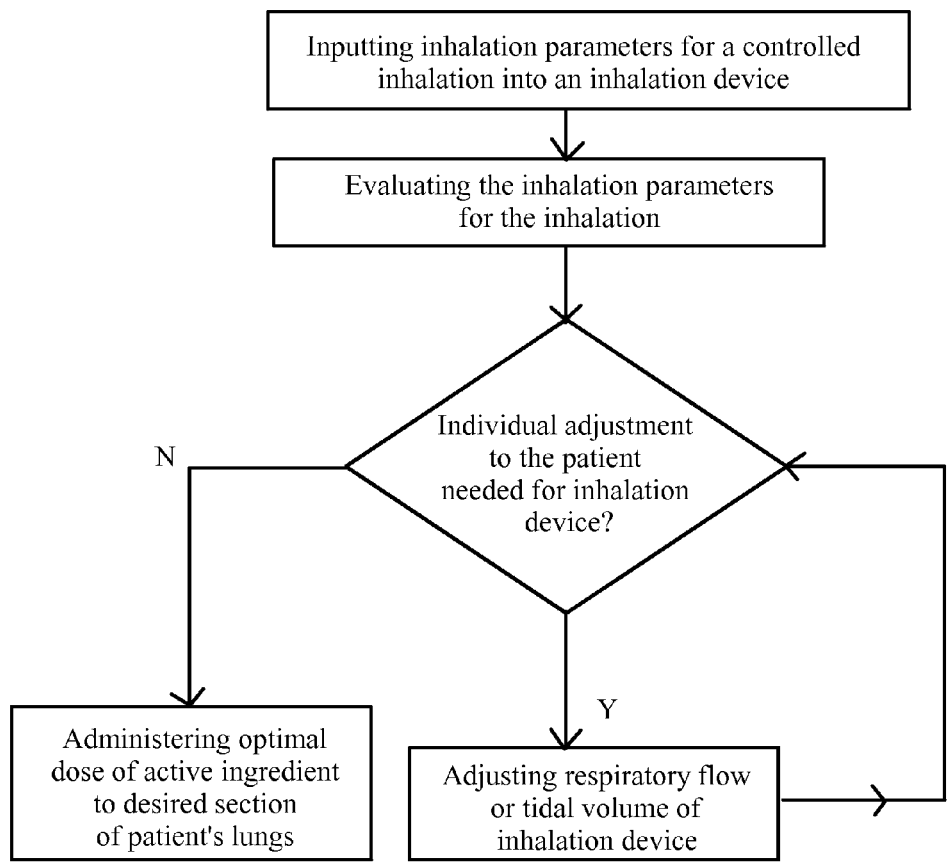
FIG. 4 shows a method of using the inhaler device in an embodiment of the present invention.

The present invention is based on the idea to provide an inhalation device with means offering individual patient parameters and/or aerosol parameters for the inhalation as well as means that adapt the dosage of the aerosol/s as a function of the predetermined individual patient and/or aerosol parameters. Thus, the inhalation device according to the invention may be individually adapted to the patient's capabilities.

According to a first embodiment, the individual parameters are provided on a memory medium 10, for example on memory media that are available under the designations SmartCard, FlashCard or SmartLabel. The individual parameters are stored in the memory medium 10 for example upon a measurement of the current pulmonary function of the patient 20 (carried out e.g. by the family doctor). According to a first embodiment, the patient 20 then inserts this medium 10 (at home) into the inhalation device 12, whereupon the individual data are read out. Alternatively, the memory medium 10 is inserted into a separate device from which the individual parameters are transferred to the inhalation device 12. According to a further alternative embodiment, a modem 14 is provided so that the inhalation device 12 is provided with the individual parameters by the physician or the institution in charge via a data link 16 (for example a telephone line).

According to a further embodiment, means for the manual data input of individual parameters are provided, e.g. by the respective keys. Alternatively, in the device 12 according to the invention, the individual parameters are adjusted via manual control units 22, e.g. potentiometers, or manual switches.

Thus, the individual patient and/or aerosol parameters influence the individual dosage of the aerosol/s either manually or automatically (e.g. via a respective valve control). Since the amount of aerosol deposition in certain lung sections dependent on the particle size of the active ingredient, the tidal volume and the respiratory flow is known, the aerosol deposition in the lung can essentially be predetermined according to the present invention. The patient 20 considers the adjusted breathing maneuver agreeable since it is adapted to his/her capabilities.

An adjusting means or mechanism adjusts individual aerosol doses administered by the device on the basis of the predetermined individual patient parameters and/or aerosol parameters. The adjusting means adjusts a respiratory flow and/or a tidal volume of the inhalation device by accessing the individual patient parameters and/or aerosol parameters for the inhalation through an input mechanism, and evaluating the parameters. On the basis of those parameters, the adjusting means adjusts respiratory flow and tidal volume of the inhalation device. One example of an adjusting means of the present invention is one or more valves controlling the amount of respiratory flow and tidal volume of the inhalation device.

In a preferred embodiment, an adjusting means for adjusting individual aerosol doses on the basis of the predetermined individual patient parameters and/or aerosol parameters by adjusting a respiratory flow and/or a tidal volume of the inhalation device is provided.

In a preferred embodiment, each breathing maneuver carried out by the patient 20 is stored on the memory medium 10 of the inhalation device 12 so that the administration may be controlled after a certain period of therapy.

In a further preferred embodiment, the memory medium 10 is reprogrammable in order to provide adapted parameters for the correct breathing maneuver if the pulmonary function of the patient 20 changes.

Preferably, the inhalation device 12 according to the present invention prevents an overdose, for example by presetting an action period or an action blockage, e.g. on the memory medium 10. This prevents the activation of the inhalation device 12 by the patient 20 as long as the necessary period of time between two successive inhalations has not lapsed. Preferably, the memory medium 10 also serves for recording errors. It records for example whether the atomizer pressure deviates too much from a desired range or whether the required atomizer pressure could not be built up at all. Moreover, the memory medium 10 preferably records a possible safety cutoff when the pressure at the mouthpiece 18 (positive pressure respiration) gets too high. In a further preferred embodiment, a too high deviation of the flow (either the atomizer flow of the aerosol or the auxiliary flow of the additional air supplied to the aerosol air or the sum of both flows) is recorded or an error message if one of the aforementioned flows for the inhalation could not be built up. Preferably, a termination of the inhalation is also recorded by the patient 20.

Preferably, the designation of the drug to be inhaled is also stored on the memory medium 10.

Moreover, according to a preferred embodiment, an access control for servicing is provided. Servicing software in the inhalation device 12 for is activated by means of a specific code in the memory medium 10.

The inhalation device according to the invention offers the following advantages:

1. For each patient 20, an individually agreeable and optimal inhalation manoeuvre is adjusted or pre-set;
2. By pre-setting individual parameters, different substances may be applied to different desired areas of the lung;
3. The release of the active ingredient is made more reproducible;
4. The optimal dose of the active ingredient is applied to the desired section of the patient's lung.
5. By programming different breathing maneuvers, different drugs may be inhaled with one device optimally and individually adapted for each patient 20;
6. The inhalation device according to the invention may immediately be updated to new substances, new breathing maneuvers and changed respiratory flows;
7. In a memory medium 10, such as a SmartCard, breathing maneuvers in the course of a therapy may be recorded and subsequently evaluated;
8. If the patient's pulmonary function changes, the inhalation device may easily be re-set to the changed basic condition;
9. The use of a propellant is not absolutely necessary.

An exemplary inhalation device that can be adapted for purposes of the present invention is disclosed in U.S. Pat. No. 5,161,524 to Evans, the disclosure of which is hereby incorporated by reference. Evans discloses a breath-actuated inhalator having a primary and a secondary air flow conduit. The portable dosage inhalator dispenses to a patient a predetermined amount of a pharmacologically active dry powder compound. The inhalator includes a housing defining an air exit end for insertion into the mouth of a patient. The inhalator also includes a primary air conduit within the housing and defining a venturi within the primary air conduit. The inhalator further includes a secondary air conduit within the housing adjacent the primary air conduit. The inhalator controls air flow velocity therethrough during inhalation by the patient. A regulator normally closes the secondary air conduit to air flow and is adapted to move between a first position where the secondary air conduit is substantially closed and a second position where the secondary air conduit is substantially open in response to air pressure differentials created in the venturi of the primary air conduit as a patient inhales through the air exit end of the housing.

According to the invention, all medicinal agents may be used which become effective either topically in the respiratory system or systemically. Suitable medicinal agents are analgesics, anti-angina agents, anti-allergic agents, antihistamines and anti-inflammatory agents, expectorants, antitussives, bronchodilators, diuretics, anticholinergics, corticoids, xanthines, oncotherapeutical agents as well as therapeutically active proteins or peptides, such as insulin and interferon.

The administration of medicinal agents for treating respiratory diseases, such as asthma, as well as prophylactics and agents for treating the mucosae of the tracheobronchial system is preferred. The administration of esters of retinol and vitamin A as described in EP-A- 0 352 412 is particularly preferred. The medicinal agents may be in their free form or in form of a pharmaceutically acceptable salt or ester. A further possibility consists in embedding the medicinal agent in liposomes.

The medicinal agents may be packaged with conventional, pharmaceutically acceptable excipients.

What is claimed is:

1. A method for administering a controlled inhalation of therapeutic aerosols for a patient during an adjusted breathing maneuvers comprising the steps of:
    inputting into an inhalation device a plurality of inhalation parameters for the inhalation;
        wherein the inhalation parameters are selected from the group consisting of:
            a) a plurality of individual patient parameters for the patient;
            b) a plurality of aerosol parameters; and
            c) a combination of a) and b);
    individually adjusting the inhalation device to the patient to be treated by adapting a dosage of at least one aerosol on the basis of the inhalation parameters to obtain a predetermined amount of aerosol deposition in a lung of the patient, comprising the substeps of:
    evaluating the inhalation parameters for the inhalation; and
    adjusting a breathing maneuver of the patient according to capabilities of the patient by adjusting a respiratory flow or a tidal volume of the inhalation device based on the inhalation parameters such that an optimal dose of at least one active ingredient of at least one aerosol is applied to a desired section of the lung of the patient during the controlled inhalation.

2. The method of claim 1, wherein the step of adjusting is accomplished using at least one valve.

3. The method of claim 1, wherein an air flow through the inhalation device is controlled based on the inhalation parameters.

4. The method of claim 1 further comprising the step of inhaling through the inhalation device by the patient.

5. The method of claim 1, wherein the step of inputting comprises the substep of receiving the inhalation parameters through a modem.

6. The method of claim 1, wherein the step of inputting comprises the substep of manually inputting the inhalation parameters.

7. The method of claim 1, further comprising the step of controlling an air flow through the inhalation device during inhalation by the patient.

8. The method of claim 1, wherein the inputting step comprises the substeps of:
   inserting a memory medium into the inhalation device; and
   storing the inhalation parameters on the memory medium before the inhalation.

9. The method of claim 8, wherein the memory medium also stores data from breathing maneuvers carried out.

10. The method of claim 8, wherein the memory medium is selected from the group consisting of:
    a) a SmartCard;
    b) a FlashCard; and
    c) a SmartLabel.

11. The method of claim 8, wherein the memory medium is reprogrammable such that the individual patient parameters stored on the memory medium are adapted if a pulmonary function of the patient changes.

12. The method of claim 8, wherein the memory medium also stores an action blockage pre-setting such that a period of time lapses between successive inhalations to prevent an overdose.

13. The method of claim 8, wherein the substep of storing the inhalation parameters on the memory medium occurs prior to the substep of inserting the memory medium into the inhalation device.

14. A method for administering a controlled inhalation of therapeutic aerosols for a patient during breathing maneuvers comprising the steps of:
   inputting into an inhalation device a plurality of individual patient parameters for the patient for the inhalation;
   individually adjusting the inhalation device to the patient to be treated by adapting a dosage of at least one aerosol on the basis of the individual patient parameters to obtain a predetermined amount of aerosol deposition in a lung of the patient, comprising the substeps of:
      evaluating the individual patient parameters for the inhalation; and
      adjusting a breathing maneuver of the patient according to capabilities of the patient by adjusting a respiratory flow or a tidal volume of the inhalation device based on the individual patient parameters such that an optimal dose of at least one active ingredient of at least one aerosol is applied to a desired section of the lung of the patient during the controlled inhalation.

15. The method of claim 14, wherein the inputting step comprises the substeps of:
   inserting a memory medium into the inhalation device; and
   storing the individual patient parameters on the memory medium before the inhalation.

16. A method for administering a controlled inhalation of therapeutic aerosols for a patient during breathing maneuvers comprising the steps of:
   inputting into an inhalation device a plurality of aerosol parameters for the inhalation;
   individually adjusting the inhalation device to the patient to be treated by adapting a dosage of at least one aerosol on the basis of the aerosol parameters to obtain a predetermined amount of aerosol deposition in a lung of the patient, comprising the substeps of:
      evaluating the aerosol parameters for the inhalation; and
      adjusting a breathing maneuver of the patient according to capabilities of the patient by adjusting a respiratory flow or a tidal volume of the inhalation device based on the aerosol parameters such that an optimal dose of at least one active ingredient of at least one aerosol is applied to a desired section of the lung of the patient during the controlled inhalation.

17. The method of claim 16, wherein the inputting step comprises the substeps of:
   inserting a memory medium into the inhalation device; and
   storing the aerosol parameters on the memory medium before the inhalation.

* * * * *

UNITED STATES PATENT AND TRADEMARK OFFICE
CERTIFICATE OF CORRECTION

PATENT NO. : 7,766,012 B2  Page 1 of 1
APPLICATION NO. : 09/810988
DATED : August 3, 2010
INVENTOR(S) : Gerhard Scheuch et al.

It is certified that error appears in the above-identified patent and that said Letters Patent is hereby corrected as shown below:

Column 4, line 32: replace "maneuvers" with "maneuver"

Signed and Sealed this

Sixteenth Day of November, 2010

David J. Kappos
*Director of the United States Patent and Trademark Office*